United States Patent [19]

Meyer et al.

[11] Patent Number: 5,041,603

[45] Date of Patent: Aug. 20, 1991

[54] N-PHENYLSULFONYL-N'-PYRIMIDINYLUREAS AND N-PHENYLSULFONYL-N'-TRIAZINYL UREAS

[75] Inventors: Willy Meyer, Riehen, Switzerland; Dieter Reinehr, Kandern, Fed. Rep. of Germany; Konrad Oertle, Therwil; Rolf Schurter, Binningen, both of Switzerland

[73] Assignee: Ciba-Geigy Corporation, Ardsley, N.Y.

[21] Appl. No.: 464,578

[22] Filed: Jan. 12, 1990

Related U.S. Application Data

[60] Continuation of Ser. No. 221,850, Jul. 20, 1988, abandoned, Division of Ser. No. 525,366, Aug. 22, 1983, Pat. No. 4,780,125.

[30] Foreign Application Priority Data

Sep. 1, 1982 [CH] Switzerland ............... 5201

[51] Int. Cl.$^5$ ............ C07C 255/09; C07C 255/07; C07C 311/16
[52] U.S. Cl. .................. 258/405; 71/92; 71/103; 558/408; 558/409; 562/870; 564/42; 564/90; 564/162
[58] Field of Search .............. 564/90; 71/103; 562/870; 558/405, 408, 409

[56] References Cited

FOREIGN PATENT DOCUMENTS 0044210 1/1982 European Pat. Off. ............... 71/92

Primary Examiner—Glennon H. Hollrah
Assistant Examiner—Susan P. Treanor
Attorney, Agent, or Firm—Kevin T. Mansfield; Edward McC. Roberts

[57] ABSTRACT

The invention relates to N-phenylsulfonyl-N'-pyrimidinylureas and N-phenylsulfonyl-N-triazinylureas of the general formula

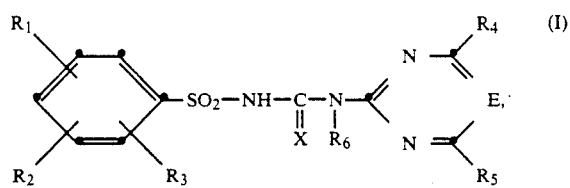

wherein
$R_1$ is hydrogen, halogen, nitro, amino, $C_1$-$C_5$alkyl, $C_1$-$C_4$haloalkyl or a —Q—$R_7$, —CO—$OR_8$ or —(CO)$_n$—$NR_9R_{10}$ radical,
$R_2$ is hydrogen, $C_1$-$C_4$alkyl, $C_1$-$C_4$alkoxy, $C_1$-$C_4$alkylthio, $C_1$-$C_4$haloalkyl, $C_1$-$C_4$haloalkoxy, halogen or alkoxyalkyl containing not more than 4 carbon atoms,
$R_3$ is $C_2$-$C_{10}$alkenyl which is substituted by one or more fluorine or bromine atoms or by one or more hydroxyl, cyano, nitro, —(Y)$_m$—CO—(Z)$_n$—$R_8$, —$SO_2$—$NR_{11}R_{12}$, —S(O)$_p$—$C_1$-$C_3$haloalkyl or —S(O)$_n$—$C_1$-$C_3$alkyl groups and which may additionally be substituted by one or more chlorine atoms,
$R_4$ is $C_1$-$C_3$alkyl, $C_1$-$C_3$haloalkyl, $C_1$-$C_3$alkoxy or $C_1$-$C_3$haloalkoxy,
$R_5$ is hydrogen, halogen, —$NR_{13}R_{14}$, $C_1$-$C_3$alkyl, $C_1$-$C_3$haloalkyl, $C_1$-$C_3$alkoxy or $C_1$-$C_2$haloalkoxy,
$R_6$ is hydrogen, $C_1$-$C_3$alkyl or $C_1$-$C_3$alkoxy,
X is oxygen or sulfur, and
E is nitrogen or the methine group, and
$R_7$ is $C_1$-$C_4$alkyl which is substituted by halogen or $C_1$-$C_3$alkoxy or is $C_3$-$C_5$alkenyl,
$R_8$ is $C_1$-$C_4$alkyl, $C_1$-$C_4$haloalkyl or $C_2$-$C_6$alkoxyalkyl,
$R_9$, $R_{10}$, $R_{11}$, $R_{12}$, $R_{13}$ and $R_{14}$, each independently of the other, are hydrogen or $C_1$-$C_3$alkyl,
Q is oxygen, sulfur, the sulfinyl or sulfonyl bridge,
Y is oxygen, sulfur or —$NR_{16}$—, wherein $R_{16}$ is hydrogen or $C_1$-$C_3$alkyl,
Z is oxygen, sulfur or —$NR_{17}$—, wherein $R_{17}$ is hydrogen or $C_1$-$C_3$alkyl,
m and n are each 0 or 1, and
p is 0, 1 or 2, and to the salts of these compounds with amines, alkali metal bases or alkaline earth metal bases.

These compounds have good pre- and postemergence selective herbicidal and growth regulating properties.

3 Claims, No Drawings

N-PHENYLSULFONYL-N'-PYRIMIDINYL-UREAS AND N-PHENYL-SULFONYL-N'-TRIAZINYL UREAS

This application is a continuation of application Ser. No. 07/221,850, filed Jul. 20, 1988, abandoned, which is a divisional of Ser. No. 06/525,366, filed Aug. 22, 1983, now U.S. Pat. No. 4,780,125.

The present invention relates to novel N-phenylsulfonyl-N'-pyrimidinylureas and N-phenylsulfonyl-N'-triazinylureas having herbicidal and growth regulating properties, to the preparation thereof, to compositions containing them, and to the use thereof of controlling weeds, in particular selectively, in crops of useful plants, or for regulating and inhibiting plant growth.

The N-phenylsulfonyl-N'-pyrimidinylureas and -N'-triazinylureas, and the salts thereof, have the general formula I

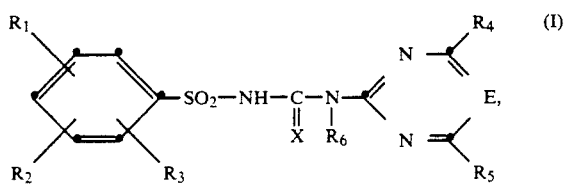

wherein
- $R_1$ is hydrogen, halogen, nitro, amino, $C_1$–$C_5$alkyl, $C_1$–$C_4$haloalkyl or a —Q—$R_7$, —CO—$OR_8$ or —(CO)$_n$—$NR_9R_{10}$ radical,
- $R_2$ is hydrogen, $C_1$–$C_4$alkyl, $C_1$–$C_4$alkoxy, $C_1$–$C_4$alkylthio, $C_1$–$C_4$haloalkyl, $C_1$–$C_4$haloalkoxy, halogen or alkoxyalkyl containing not more than 4 carbon atoms,
- $R_3$ is $C_2$–$C_{10}$alkenyl which is substituted by one or more fluorine or bromine atoms or by one or more hydroxyl, cyano, nitro, —(Y)$_m$—CO—(Z)$_n$—$R_8$, —$SO_2$—$NR_{11}R_{12}$, —S(O)$_p$—$C_1$–$C_3$haloalkyl or —S(O)$_n$—$C_1$–$C_3$alkyl groups and which may additionally be substituted by one or more chlorine atoms,
- $R_4$ is $C_1$–$C_3$alkyl, $C_1$–$C_3$haloalkyl, $C_1$–$C_3$alkoxy or $C_1$–$C_3$haloalkoxy,
- $R_5$ is hydrogen, halogen, —$NR_{13}R_{14}$, $C_1$–$C_3$alkyl, $C_1$–$C_3$haloalkyl, $C_1$–$C_3$alkoxy or $C_1$–$C_2$haloalkoxy,
- $R_6$ is hydrogen, $C_1$–$C_3$alkyl or $C_1$–$C_3$alkoxy,
- X is oxygen or sulfur, and
- E is nitrogen or the methine group, and
- $R_7$ is $C_1$–$C_4$alkyl which is substituted by halogen or $C_1$–$C_3$alkoxy or is $C_3$–$C_5$alkenyl,
- $R_8$ is $C_1$–$C_4$alkyl, $C_1$–$C_4$haloalkyl or $C_2$–$C_6$alkoxyalkyl,
- $R_9$, $R_{10}$, $R_{11}$, $R_{12}$, $R_{13}$ and $R_{14}$, each independently of the other, are hydrogen or $C_1$–$C_3$alkyl,
- Q is oxygen, sulfur, the sulfinyl or sulfonyl bridge,
- Y is oxygen, sulfur or —$NR_{16}$—, wherein $R_{16}$ is hydrogen or $C_1$–$C_3$alkyl,
- Z is oxygen, sulfur or —$NR_{17}$—, wherein $R_{17}$ is hydrogen or $C_1$–$C_3$alkyl,
- m and n are each 0 or 1, and
- p is 0, 1 or 2.

Herbicidally active ureas, triazines and pyrimidines are generally known in the art. Arylsulfamoyl-heterocyclyl-aminocarbamoyl compounds with herbicidal and plant growth-regulating action are described e.g. in European patent application 44 210, German Offenlegungsschrift 2 715 786 or in Netherlands patent specification 121 788.

In the above definitions, alkyl denotes straight-chain or branched alkyl, e.g. methyl, ethyl, n-propyl, isopropyl, the four isomers of butyl, n-amyl, isoamyl, 2-amyl, 3-amyl, n-hexyl or isohexyl.

Alkoxy denotes methoxy, ethoxy, n-propoxy, isopropoxy and the four isomers of butoxy, with methoxy, ethoxy or isopropoxy being preferred.

Alkylthio is e.g. methylthio, ethylthio, n-propylthio, isopropylthio and n-butylthio, with methylthio and ethylthio being preferred.

Alkenyl radicals are e.g. vinyl, allyl, isoprenyl, propen-1-yl, buten-1-yl, buten-2-yl, buten-3-yl, isobuten-1-yl, isobuten-2-yl, penten-1-yl, penten-2-yl, penten-3-yl and penten-4-yl, with vinyl, allyl and penten-4-yl being preferred.

Alkylsulfinyl radicals are for example methylsulfinyl, ethylsulfinyl, n-propylsulfinyl and n-butylsulfinyl, with methylsulfinyl and ethylsulfonyl being preferred.

Alkylsulfonyl is for example methylsulfonyl, ethylsulfonyl, n-propylsulfonyl and n-butylsulfonyl, with methylsulfonyl and ethylsulfonyl being preferred.

Halogen in the above definitions, as well as moiety of haloalkyl, haloalkoxy, haloalkylsulfonyl, haloalkylsulfinyl and haloalkylthio, is fluorine, chlorine and bromine, with fluorine and chlorine being preferred.

The invention also comprises the salts which the compounds of formula I are able to form with amines, alkali metal bases and alkaline earth metal bases, or with quaternary ammonium bases.

Preferred salt-forming alkali metal hydroxides and alkaline earth metal hydroxides are the hydroxides of lithium, sodium, potassium, magnesium or calcium, most preferably those of sodium or potassium.

Examples of suitable salt-forming amines are primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline. Preferred amines are ethylamine, propylamine, diethylamine or triethylamine, with isopropylamine and diethanolamine being most preferred.

Examples of substituted alkenyl radicals corresponding to the definition of the substituent R within the scope of formula I are: 3-fluoro-1-propen-1-yl, 1-fluromethylvinyl, 1-difluoromethylvinyl, 1-trifluoromethylvinyl, 3,3-difluoro-1-propen-1-yl, 3,3,3-trifluoro-1-propen-1-yl, 2,2-difluorovinyl, perfluorovinyl, 3-bromo-1-propen-1-yl, 3-cyano-1-propen-1-yl, 3-hydroxy-1-propen-1-yl, 3-chloro-3,3-difluoro-1-propen-1-yl, 3,3-dichloro-3-fluor-1-propen-1-yl, 3-fluoro-1-buten-1-yl, 3-acetoxy-1-propen-1-yl, 2-methoxyvinyl, 1,2-dibromo-1-propen-1-yl, 2-methoxycarbonylvinyl, 2-ethoxycarbonyl-1-propen-1-yl, 1-chloro-3,3,3-trifluoro-1-propen-1-yl, 3,3-difluoro-1-propen-1-yl, 2-nitrovinyl, 2-(N,N-dimethylsulfamoyl)vinyl, 2-methylsulfonylvinyl, 2-cyanovinyl, 2-ethoxycarbonylvinyl or 2-cyano-1-propene.

Preferred are haloalkenyl radicals, in particular fluoroalkenyl radicals and monosubstituted alkenyl radicals containing not more than 5 carbon atoms, the double bond of which radicals is attached direct to the phenyl nucleus. Examples of such preferred alkenyl radicals are: 3,3,3-trifluoro-1-propen-1-yl, 3-cyano-1-propen-1-yl, 3-acetoxy-1-propen-1-yl, 2-cyanovinyl, 2-cyano-1-propen-1-yl, 3-hydroxy-1-propen-1-yl, 3,3-difluoro-1-propen-1-yl, 2-methoxycarbonylvinyl and 2-ethoxy carbonylvinyl.

Examples of quaternary ammonium bases are, in general, the cations of haloammonium salts, e.g. the tetramethylammonium cation, the trimethylbenzylammonium cation, the triethylbenzylammonium cation, the tetraethylammonium cation, the trimethylethylammonium cation, and also the ammonium cation.

Preferred compounds of the formula I are those in which either a) X is oxygen, or
b) $R_3$ and $R_4$ together contain not more than 4 carbon atoms, or
c) $R_6$ is hydrogen, or
d) $R_1$ and $R_2$ are hydrogen, or
e) $R_3$ is a substituted $C_2-C_{10}$alkenyl group which is attached at the olefinic group to the phenyl nucleus, or
f) $R_3$ is in the 2-position to the sulfonyl group.

Preferred compounds of group e) are those in which the substituted alkenyl group contains 2 to 4 carbon atoms.

Especially preferred substituents at the alkenyl group are: fluorine, bromine, nitro, cyano, methoxy, methoxycarbonyl, methylcarbonyl, ethoxycarbonyl, hydroxyl, acetoxy, methylsulfonyl, trifluoromethylsulfonyl, trifluoromethylsulfinyl or dimethylsulfamoyl, with fluorine, cyano, acetoxy, bromine and hydroxyl being most preferred.

Particularly preferred subgroup of compounds of the formula I comprises those compounds in which X is oxygen and $R_1$, $R_2$ and $R_6$ are hydrogen, $R_4$ and $R_5$ together contain not more than 4 carbon atoms, $R_3$ is in the 2-position to the sulfonyl group and is a $C_2-C_4$alkenyl group which is attached at the olefinic group to the phenyl nucleus and is substituted by fluorine, bromine, nitro, cyano, methoxy, acetoxy, methoxycarbonyl, ethoxycarbonyl, hydroxy, trifluoromethylsulfonyl, trifluoromethylsulfinyl, methylsulfonyl or dimethylsulfamoyl.

Compounds of this preferred subgroup meriting special attention are those in which the substituents of the substituted alkenyl group $R_3$ are fluorine, cyano, acetoxy, bromine or hydroxyl.

Prefered individual compounds are:

N-[2-(3,3,3-trifluoro-1-propen-1-yl)phenylsulfonyl]-N'-(4-methoxy-6-methyl-1,3,5-triazin-2-yl)urea,
N-[2-(3,3,3-trifluoro-1-propen-1-yl)phenylsulfonyl]-N'-(4,6-dimethoxy-1,3,5-triazin-2-yl)urea and
N-[2-(2-bromovinyl)phenylsulfonyl]-N'-[4-methoxy-6-methyl-1,3,5-triazin-2-yl)urea.

A first process for obtaining the compounds of the formula I comprises reacting a phenylsulfonamide of the formula II

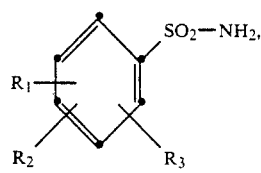

wherein $R_1$, $R_2$ and $R_3$ are as defined for formula I, with an N-pyrimidinylcarbamate or N-triazinylcarbamate of the formula III

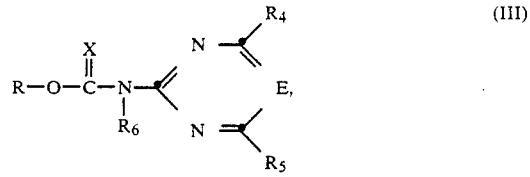

wherein E, $R_4$, $R_5$, $R_6$ and X are as defined for formula I, and R is phenyl, alkyl or substituted phenyl, in the presence of a base.

In another process, compounds of formula I are obtained by reacting a phenylsulfonyl isocyanate or phenylsulfonyl isothiocyanate of the formula IV

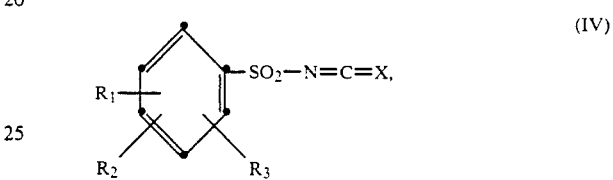

wherein $R_1$, $R_2$, $R_3$ and X are as defined for formula I, with an amine of the formula V

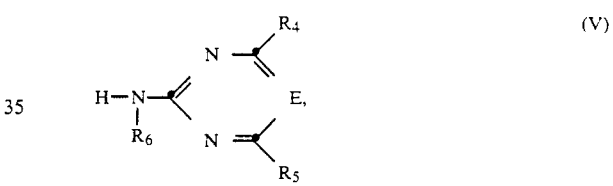

wherein E, $R_4$, $R_5$ and $R_6$ are as defined for formula I, optionally in the presence of a base.

A further process for obtaining the compounds of formula I comprises reacting a sulfonamide of the formula II above with an isocyanate or isothiocyanate of the formula VI

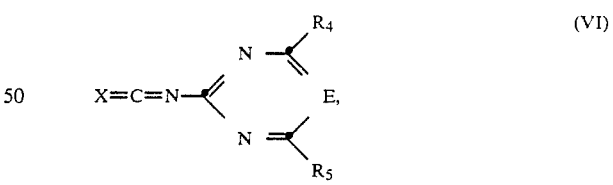

wherein E, $R_4$, $R_5$ and X are as defined for formula I, optionally in the presence of a base.

Finally, the compounds of formula I can also be obtained by reacting an N-phenylsulfonylcarbamate of the formula VII

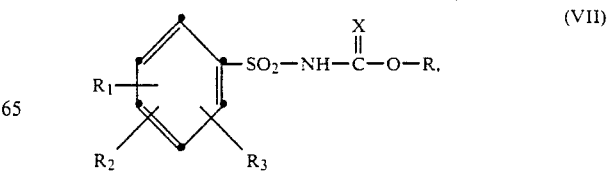

wherein $R_1$, $R_2$, $R_3$ and X are as defined for formula I and R is phenyl, alkyl or substituted phenyl, with an amine of formula V above.

If desired, the ureas of the formula I can be converted into salts with amines, alkali metal hydroxides or alkaline earth metal hydroxides, or with quaternary ammonium bases. This conversion is carried out e.g. by reacting the compounds of formula I with the equimolar amount of a base and removing the solvent by evaporation.

The reactions for obtaining the compounds of formula I are conveniently carried out in aprotic, inert organic solvents such as methylene, chloride, tetrahydrofuran, acetonitrile, dioxan or toluene.

The reaction temperatures are preferably in the range from $-20°$ to $+120°$ C. The coupling reactions are normally slightly exothermic and can be carried out at room temperature. To shorten the reaction time or also to initiate the reaction it is expedient to heat the reaction mixture briefly to boiling point. The reaction times can also be shortened by addition of a few drops of a base or isocyanate as catalyst.

The final products can be isolated by concentrating the reaction mixture and/or removing the solvent by evaporation, and by recrystallisation or by triturating the solid residue in a solvent in which it is poorly soluble, e.g. an ether, an aromatic hydrocarbon or a chlorinated hydrocarbon.

The compounds of formula I are stable compounds and no precautionary measures are necessary for handling them.

Some of the starting materials of the formula II, IV and VII are novel and can be prepared by the following methods.

For example, the novel intermediates of the narrower formula IIa

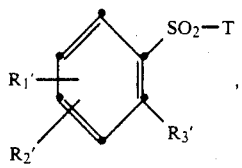

(IIa)

wherein

T is hydroxyl, —OM,

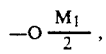

Cl, —N=C=O or —NHT$_4$, where M is an alkali metal atom and $M_1$ is an alkaline earth metal atom, $R_1'$ is hydrogen, halogen, $C_1$-$C_5$alkyl, $C_1$-$C_4$haloalkyl, $C_1$-$C_4$alkoxy, —COOR$_8$, —CONR$_9$R$_{10}$ or —NO$_2$, $R_2'$ is hydrogen, halogen, $C_1$-$C_4$alkyl, $C_1$-$C_4$haloalkyl, $C_1$-$C_4$alkoxy, $C_1$-$C_4$haloalkoxy or alkoxyalkyl containing not more than 4 carbon atoms, $R_3'$ is a —C(T$_1$)=C(T$_2$) (T$_3$) group, $T_1$ is hydrogen, $C_1$-$C_4$alkyl, cyano, or —COO—C$_1$-$C_4$alkyl, $T_2$ is a —COOR$_8$, —CONR$_9$R$_{10}$, —CH$_2$—COOR$_8$, —CH$_2$—C$_1$-$C_4$alkoxy, —CH(C$_1$-$C_4$alkyl)—C$_1$-$C_4$alkoxy, —CH$_2$—CN, —CH$_2$—O—CO—CH$_3$, —CH(C$_1$-$C_4$alkyl)—O—CO—CH$_3$, —S(O)$_q$—C$_1$-$C_3$alkyl, —S(O)$_q$—C$_1$-$C_3$haloalkyl, where q is 0, 1 or 2, —COR$_8$, —CH$_2$—CH(COOR$_8$)$_2$ or $C_1$-C$_8$alkyl which is substituted by one or more fluorine or bromine atoms, $T_3$ is hydrogen, —COO—C$_1$-$C_4$alkyl or $C_1$-$C_5$alkyl which is unsubstituted or substituted by halogen atoms, and $T_4$ is hydrogen, —CO—NH—C$_1$-$C_4$alkyl, —COO—C$_1$-$C_4$alkyl or —COO-phenyl, the alkyl groups $T_1$, $T_2$ and $T_3$ together containing not more than 8 carbon atoms and $R_8$, $R_9$ and $R_{10}$ being as defined for formula I, with the proviso that $T_2$ is not —COO—C$_1$-$C_4$alkyl if at the same time $R_1$, $R_2$, $T_1$ and $T_3$ are hydrogen and T is the amino group, are obtained by diazotising an amine of the formula VIII

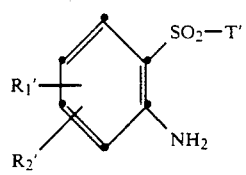

(VIII)

to a diazonium salt of the formula IX

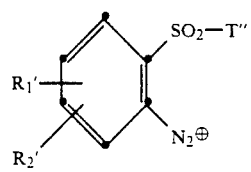

(IX)

reacting said diazonium salt with a compound of the formula X $$H—R_3' \quad (X)$$

in the presence of a palladium catalyst which forms a Pd(O) compound under the reaction conditions, and optionally in the presence of a base, to a compound of the formula XI

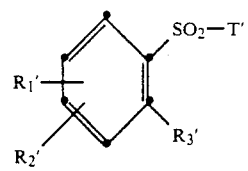

(XI)

converting the compound of formula XI, in known manner, into the corresponding sulfonyl chloride by treatment with a chlorinating agent such as thionyl chloride or PCl$_5$, treating the sulfonyl chloride with ammonia and, if desired, converting the compound of formula IIa so obtained, wherein T is —NH$_2$, into a compound of the formula IIa, wherein T$_4$ is not hydrogen, e.g. by reaction with an acylating agent O=C=N—C$_1$-C$_4$alkyl, ClCONH—C$_1$-C$_4$alkyl, ClCOO—C$_1$-C$_4$alkyl, ClCOO—phenyl, or in the presence of a C$_1$-C$_4$alkylisocyanate, and T' is OH, OM or

T'' is OM or

and M, $M_1$, $R_1'$, $R_2$ and $R_3'$ are as defined for formula IIa.

The diazotisation may be carried out by methods which are known per se in an acidic aqueous medium such as aqueous HCl, $H_2SO_4$, $H_2O$/acetic acid. The reaction of the diazonium salts with the olefins is conveniently carried out in the presence of an inert organic solvent. Examples of suitable solvents are aliphatic monocarboxylic acids or chlorinated aliphatic monocarboxylic acids, preferably acetic acid, chloroacetic acid, dichloroacetic acid or trifluoroacetic acid, acetone, dichloromethane and acetonitrile or mixtures of such solvents. It is preferred to use acetic acid.

Suitable palladium catalysts and bases are for example those of the kind described in European patent application 40177. Preferred palladium catalysts are $PdCl_2$, $[PdCl_4]Na_2$ or $[PdCl_4]Li_2$, and, in particular, bis(dibenzylideneacetone) palladium(O). Preferred bases are alkali metal carboxylates such as sodium acetate. In general, it is not necessary to isolate the diazonium salts of the formula IX and the sulfonyl chlorides. If the diazotisation is carried out in the presence of acetic acid and of only one equivalent of a strong acid, and if the diazonium salts are further used without isolation, then the addition of a base can usually be omitted in the reaction with the olefins of the formula X.

Compounds of the formula IIa, wherein $R_1'$ and $R_2'$ are not bromine or iodine, can also be prepared by reacting a compound of the formula XII

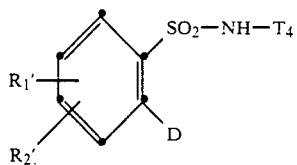

with an olefin of the formula X, wherein $R_1'$, $R_2'$ and $T_4$ are as defined for formula IIa and D is bromine or iodine, in the presence of a palladium catalyst which may contain arsenic or phosphorous and of a base.

Examples of suitable palladium catalysts and bases for this process variant are compounds of the kind described in U.S. Pat. No. 3,922,299. It is preferred to use mixtures of palladium acetate and triphenylphosphine or tri-o-tolylphosphine as catalysts. If D in formula X is iodine, then it is also possible to use palladium compounds which do not contain arsenic or phosphorus, in particular palladium acetate. Suitable bases are in particular trialkylamines, preferably triethylamine or tri-n-butylamine, and alkali metal carboxylates, preferably sodium acetate.

The palladium catalysts are advantageously used in both process variants in an amount of about 0.01 to 5 mole %, based on the diazonium salt of the formula IX or the halobenzene of the formula XII.

The reaction of the halobenzenes of the formula XII with the olefins of the formula X is also advantageously carried out in the presence of an inert organic solvent, e.g. an aromatic hydrocarbon or a halogenated aromatic hydrocarbon such as toluene, xylene or chlorobenzene, or an N,N-dialkylamide of an aliphatic monocarboxylic acid of the kind mentioned above, in particular N,N-dimethylformamide.

The other novel intermediates of the formula II can basically be obtained in accordance with two different synthesis routes which can be carried out by known methods.

For example, the sulfonamides of the formula II are obtained from corresponding benzosulfonamides by introducing the alkenyl side chain, or by modifying an existing side chain, by known methods. Corresponding processes are disclosed in European patent application 44210.

The sulfonamides of the formula II are also obtained by diazotising corresponding substituted anilines and converting the diazotised compounds into the sulfonamides with sulfur dioxide and ammonia. Corresponding processes are disclosed in European patent application 44807.

Other sulfonamides of the formula II are obtained by chlorinating appropriately substituted thiobenzyl ethers and treating the sulfochlorides so obtained with ammonia. Corresponding processes are disclosed in European patent application 41404.

The starting materials of the formulae III, V, VI, VIII and XII are known or they can be prepared in a manner known per se.

The compounds of the formulae IV and VII can be prepared in a manner known per se from the compounds of the formula II or IIa.

The phenylsulfonylisocyanates of the formula IV can be obtained by phosgenating the sulfonamides of the formula II, in the presence of butylisocyanate, in a chlorinated hydrocarbon as solvent, at reflux temperature. Similar reactions are described in "Newer Methods of Preparative Organic Chemistry", Vol. VI, 223–241, Academic Press, New York and London.

The isothiocyantes of the formula IV are obtained by treating the sulfonamides of formula II with carbon disulfide and potassium hydroxide and by subsequent phosgenation of the dipotassium salt. Such processes are described in Arch. Pharm. 299, 174 (1966).

The N-phenylsulfonylcarbamates of the formula VII are obtained by reacting the sulfonamides of the formula II with diphenyl carbonate in the presence of a base. Similar processes are described in Japanese patent specification 61 169.

Novel compounds of the formulae III and VI can be prepared by known methods, from corresponding compounds of the formula V.

Novel fluoroalkoxyaminopyrimidines and fluoroalkoxyaminotriazines of the formula V, the preparation thereof and the preparation of corresponding compounds of the formula III and IV therefrom, are described in European patent application 70804.

Isocyanates of the formula VI can be prepared by reacting amines of the formula V with oxalyl chloride in a chlorinated hydrocarbon as solvent. Amines of the formula V are known and some are commercially available, or they can be prepared by known methods, q.v. "The Chemistry of Heterocyclic Compounds", Vol. XIV, Interscience Publishers, New York, London.

The compounds of formula IIa are novel and have been specially developed for the synthesis of the compounds of formula I. They therefore also constitute an object of the present invention.

In formula IIa, it is preferred that at least one of $T_1$ and $T_3$, preferably $T_1$, is hydrogen. T is preferably —NH$_2$ and R$_1$', R$_2$' and R$_3$' have the meanings assigned to R$_1$, R$_2$ and R$_3$ for formula I.

When used at low rates of application, the compounds of formula I have good selective growth inhibiting and selective herbicidal properties which make them most suitable for use in crops of useful plants, especially in cereals, cotton, soybeans, maize and rice. In some cases damage is also caused to weeds which have only been controlled up to now with total herbicides.

The mode of action of these compounds is unusual. Many are translocatable, i.e. they are absorbed by the plant and transported to other parts of it where they then exert their action. Thus, for example, it is possible to damage perennial weeds to the roots by surface treatment. Compared with other herbicides and growth regulators, the novel compounds of the formula I are effective even when used at very low rates of application.

The compounds of formula I have in addition pronounced growth-regulating, especially growth-inhibiting, properties. The growth of both monocots and dicots is inhibited.

Inhibition of the vegetative growth of may cultivated plants permits more plants to be sown in a crop area, so that a higher yield may be obtained per unit or area. A further mechanism of yield increase using growth regulators resides in the fact that nutrients are able increasingly to promote flower formation and fruiting, whilst vegetative growth is inhibited.

Thus, for example, the compounds of formula I are able to inhibit selectively the growth of leguminosae which are frequently planted as cover crops in tropical regions, so that, while soil erosion between cultivated plants is prevented, the cover crops cannot compete with the cultivated plants.

Further, the compounds of formula I are suitable for preventing stored potatoes from seeding. During winter storage, potatoes often develop sprouts which result in shrinkage, weight loss, and rot.

At higher rates of application, all tested plants are so severely damaged in their development that they die.

The invention also relates to herbicidal and growth-regulating compositions which contain a novel compound of the formula I, and also to methods of controlling weeds pre- and postemergence and of inhibiting the growth of monocots and dicots, especially grasses, tropical cover crops and tobacco plant suckers.

The compounds of the formula I are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering or pouring, are chosen in accordance with the intended objectives and the prevailing circumstances.

The formulations, i.e. the compositions containing the compound (active ingredient) of the formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethylsulfoxide or dimethylformamide, as well as epoxidised vegetable oils such as epoxidised coconut oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of the formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammoniums salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsufonates are the sodium, calcium or triethylanolamine salts of naphthalenesulfonic acid/formaldehyde condensation product. Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8$–$C_{22}$alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in the following publications: "McCutcheon's Detergents and Emulsifiers Annual", MC Publishing Corp. Ridgewood, N.J., 1981; H. Stache, "Tensid-Taschenbuch", 2nd Edition, C. Hanser Verlag, Munich & Vienna, 1981; M and J. Ash, "Encyclopedia of Surfactants", Vol. I-III, Chemical Publishing Co., New York, 1980-81.

The pesticidal compositions usually contain 0.1 to 95%, preferably 0.1 to 80%, of a compound of the formula I,
1 to 99.9%, of a solid or liquid adjuvant, and 0 to 25%, preferably
0.1 to 25%, of a surfactant.

Preferred formulations are composed in particular of the following constituents (%=percent by weight):

| Emulsifiable concentrates | |
|---|---|
| active ingredient: | 1 to 20%, preferably 5 to 10% |
| surfactant: | 5 to 30%, preferably 10 to 20% |
| liquid carrier: | 50 to 94%, preferably 70 to 85% |
| Dusts | |
| active ingredient: | 0.1 to 10%, preferably 0.1 to 1% |
| solid carrier: | 99.9 to 90%, preferably 99.9 to 99% |
| Suspension concentrates | |
| active ingredient: | 5 to 75%, preferably 10 to 50% |
| water: | 94 to 25%, preferably 90 to 30% |
| surfactant: | 1 to 40%, preferably 2 to 30% |
| Wettable powders | |
| active ingredient: | 0.5 to 90%, preferably 10 to 80% |
| surfactant: | 0.5 to 20%, preferably 1 to 15% |
| solid carrier: | 5 to 95%, preferably 15 to 90% |
| Granulates | |
| active ingredient: | 0.5 to 30%, preferably 3 to 15% |
| solid carrier: | 99.5 to 70%, preferably 97 to 85%. |

Whereas commercial products will be preferably formulated as concentrates, the end user will normally employ dilute formulations. The formulations can be diluted to a concentration as low as 0.001%. The rates of application are normally from 0.01 to 10 kg a.i./ha, preferably from 0.025 to 5 kg a.i./ha.

The compositions may also contain further ingredients, such as stabilisers, antifoams, viscosity regulators, binders, tackifiers as well as fertilisers or other active ingredients in order to obtain special effects.

PREPARATORY EXAMPLES

EXAMPLE 1

N-[2-(3,3,3-trifluoro-1-propen-1-yl)-phenylsulfonyl]-N'-(4-methoxy-6-methyl-1,3,5-triazin-2-yl)urea 5.2 g of N-(4-methoxy-6-methyl-1,3,5-triazin-2-yl)-phenylcarbamate are added to a solution of 5 g of 2-(3,3,3-trifluoro-1-propen-1-yl)-phenylsulfonamide and 3.3 g of 1,5-diazabicyclo[5,4,0]undec-5-one in 80 ml of dioxan, and the mixture is stirred for 3 hours at 20°–25° C. The clear reaction solution is then taken up in 300 ml of water and the aqueous solution is acidified with 2N hydrochloric acid to pH 4–5. The resinous precipitate is extracted from the aqueous phase with ethyl acetate and the organic extract is dried and concentrated. The oily residue is crystallised from a 1:10 mixture of acetone/ether, affording 7.2 g of the title compound with a melting point of 159°–160° C.

EXAMPLE 2

N-[2-(3-cyano-1-propen-1-yl)phenylsulfonyl]-N'-(4-methoxy-6-methyl-1,3,5-triazin-2-yl)urea.

5.2 g of N-(4-methoxy-6-methyl-1,3,5-triazin-2-yl)phenylcarbamate are added to a solution of 4.45 g of 2-(3-cyano-1-propen-1-yl)phenylsulfonamide and 3.3 ml of 1,5-diazabicyclo[5,4,0]undec-5-ene in 80 ml of dioxan, and the mixture is stirred for 15 hours at 20°–25° C. The reaction mixture is then taken up in 350 ml of water and the aqueous solution is acidified to pH 2 with 2N HCl and extracted with ethyl acetate. The organic extracts are combined and concentrated. The oily orange-coloured residue is dissolved in a very small amount of acetone. About 20 ml of diethyl ether are added to this solution, which is diluted dropwise with hexane until the onset of crystallisation. The mixture is subsequently further cooled and the precipitated crystals are isolated by filtration. Yield: 5.2 g of the title compound with a melting point of 142°–143° C.

EXAMPLE 3 a) Orthanilic Acid, Diazonium Salt 36.64 g (0.2 mole) of orthanilic acid are suspended in 30 ml of water. To this suspension are added 62.3 ml (0.5 mole) of 50% borofluoric acid and the mixture is cooled to 0°–5° C. A solution of 13.8 g (0.2 mole) of sodium nitrite in 20 ml of water is then added dropwise, with stirring, at this temperature over 1 hour. Stirring is continued for 30 minutes, 100 ml of diethyl ether are added, and the cooled suspension is filtered. The isolated solid diazonium salt is additionally washed with 100 ml of a 1:1 mixture of acetic acid and diethyl ether and subsequently with 100 ml of diethyl ether, then dried briefly in the air. Yield: 34 g (92% of theory) of diazonium salt. Concentrated hydrochloric or sulfuric acid may also be used instead of borofluoric acid without any diminution of yield.

b) 2-(1-Buten-3-on-1-yl)phenylsulfonic acid, sodium salt. 21.91 g (0.328 mole) of sodium acetate and 0.942 g ($1.64 \times 10^{-3}$ moles) of bis(dibenzylideneacetone) palladium (0) are added to 60.38 g (0.328 mole) of the diazonium salt of orthanilic acid in 500 ml of acetic acid. Then 27.6 g (0.394 mole) of methyl vinyl ketone are added slowly dropwise at room temperature. The temperature of the reaction mixture is kept at 30°–35° C. by external cooling. Two hours after the addition of the methyl vinyl ketone is complete, the product is precipitated by addition of 600 ml of ethanol. The precipitate is isolated by filtration and the residue is recrystallised from methanol/ethanol and dried in a high vacuum, affording 61.07 g (0.229 mole) of the title compound with a melting point of >250° C.

EXAMPLE 4

2-(3,3,3-trifluoro-1-propen-1-yl)phenylsulfonamide 8.06 g (0.0438 mole) of the diazonium salt of orthanilic acid are suspended in 150 ml of acetic acid and to this suspension are added 3.59 g (0.0438 mole) of sodium acetate. After addition of 0.256 g ($4.38 \times 10^{-4}$ moles) of bis(benzylideneacetone) palladium (0), the reaction vessel (250 ml Fischer-Porter flask/pressure apparatus) is evacuated once. Then 6 g (0.0625 mole) of 3,3,3-trifluoropropene are introduced under pressure. With efficient stirring the reaction commences immediately accompanied by evolution of nitrogen (rise in pressure to about 8 bar) and rise in temperature (to a maximum of about 45° C.) and is complete after about 90 minutes. The solvent is stripped off by rotary evaporation.

The residue (9.96 g) is dissolved in 50 ml of N,N-dimethylformamide and then 6.61 ml (0.0909 mole) of thionyl chloride are added dropwise. After it has been stirred for 2 hours at room temperature, the reaction mixture is poured onto ice and the sulfonyl chloride is isolated by filtration. Yield: 6.37 g. The sulfonyl chloride is dissolved direct in 20 ml of ethyl acetate, and 25 ml of conc. ammonia are added dropwise at 0°–5° C. When the reaction of the sulfonyl chloride is complete, the reaction mixture is diluted with water and extracted repeatedly with ethyl acetate. The combined ethyl acetate phases are dried and 5.35 g of product are isolated therefrom and purified by chromatography on silica gel or by recrystallisation from ethyl acetate/n-hexane. Yield: 5.08 g (0.0239 moles) of 2-(3,3,3-trifluoro-1-propen-1-yl)phenylsufonamide, corresponding to 54% of theory, based on the diazonium salt. Melting point: 153°–154° C.

Analysis: $C_9H_8F_3NO_2S$ (251,22): cal.: C 43.03, H 3.21, F 22.69, N 5.58, S 12.76. found: C 42.99, H 3.29, F 22.73, N 5.53, S 12.97.

EXAMPLE 5

2-(2-perfluorohexylvinyl)phenylsulfonamide 16.4 g (0.089 mole) of the diazonium salt of orthanilic acid are suspended in 100 ml of acetic acid. To this suspension are added 7.31 g (0.89 mole) of sodium acetate, followed by 0.5116 g ($8.9 \times 10^{-4}$ moles) of bis(benzylideneacetone)palladium(0). Then 34.61 g (0.098 mole) of 85% perfluorohexylethylene are added dropwise at room temperature. The exothermic reaction commences immediately with evolution of $N_2$. The reaction temperature is kept at 30°–40° C. by external cooling and altering the rate of dropwise addition. When the reaction is complete, the acetic acid is removed as completely as possible by rotary evaporation with the addition of toluene. The residue is converted as described in Example 4, without purification, into the corresponding sulfonamide via the sulfonyl chloride. Purification by chromatography on silica gel yields 30.28 g (0.059 mole) of 2-(2-perfluorohexylvinyl)-phenylsulfonamide, corresponding to 67% of theory (based on the diazonium salt). Melting point: 60°–61° C.

EXAMPLE 6

2-(3-acetoxy-1-buten-1-yl)phenylsulfonamide

Following the procedure of Example 5, 10 g (0.0372 mole) of 2-(3-acetoxy-1-buten-1-yl)benzenesulfonamide, with a melting point of 67°–69° C., are obtained in a yield of 45% of theory from 15.08 g (0.082 mole) of the diazonium salt of orthanilic acid, 6.72 g (0.082 mole) of sodium acetate, 9.34 g (0.082 mole) of 3-acetoxybut-1-ene and 1.882 g ($3.28 \times 10^{-3}$ moles) of bis(benzylideneacetone)palladium (0), and after conversion of the sulfonic acid sodium salt into the corresponding sulfonamide.

Analysis: $C_{12}H_{15}NO_4S$ (269.32): cal.: C 53.52, H 5.62, N 5.20, S 11.91. found: C 53.50, H 5.72, N 5.22, S 11.69.

EXAMPLE 7

2-(3-acetoxy-1-propen-1-yl)phenylsulfonamide

Following the procedure of Example 5, 14.77 g (0.08 mole) of the diazonium salt of orthanilic acid, 6.56 g (0.08 mole) of sodium acetate, 9.22 g (0.92 mole) of allyl acetate and 1.148 g ($2 \times 10^{-3}$ mole) of bis(benzylideneacetone)palladium (0) are reacted to give 25.4 g of crude product as evaporation residue. This crude product is suspended in 175 ml of chloroform and then 60 g (0.29 mole) of $PCl_5$ are added in portions. The mixture is stirred at room temperature for 2 hours and then poured onto ice. The sulfonyl chloride is extracted with a total of 400 ml of chloroform. The organic phase is washed repeatedly with a saturated solution of sodium bicarbonate, dried, and concentrated to a volume of about 150 ml by rotary evaporation. The chloroform solution is subsequently added dropwise at 0°–10° C. to 40 ml of a semiconcentrated solution of ammonia. The mixture is stirred at room temperature until the sulfonyl chloride is completely reacted to the sulfonamide. The chloroform phase is separated and the aqueous phase is extracted twice with ethyl acetate. The combined organic phases are dried and concentrated by rotary evaporation. The residue is chromatographed on silica gel, affording 7.0 g (0.0274 mole) of 2-(3-acetoxy-1-propen-1-yl)phenylsulfonamide, corresponding to a yield of 34% of theory. Melting point: 94°–95° C.

Analysis: $C_{11}H_{13}NO_4S$ (255,29): cal.: C 51.75, H 5.13, N 5.49, S 12.56. found: C 51.93, H 5.14, N 5.52, S 12.33.

EXAMPLE 8

2-(3-cyano-1-propen-1-yl)phenylsulfonamide

Following the procedure of Example 5, 114.28 g (evolution of gas corresponding to a reaction of about 75–80%) of crude 2-(3-cyano-1-propen-1-yl)phenylsulfonic acid, sodium salt, is obtained from 71.1 g (0.3854 mole) of the diazonium salt of orthanilic acid, 31.69 g (0.3864 mole) of sodium acetate, 1.58 g ($2.7 \times 10^{-3}$ moles) of bis(benzylideneacetone) palladium (0) and 31.11 g (0.463 mole) of allyl cyanide.

The residue is dissolved in 250 ml of N,N-dimethylformamide and reaction is carried out with 70.3 ml (0.966 mole) of thionyl chloride and then with ammonia. Chromatography of the residue on silica gel affords 9.75 g (0.0439 mole) of 2-(3-cyano-1-propen-1-yl)benzenesulfonamide, corresponding to a yield of 11% of theory.

Melting point: 144°–145° C.

Analysis: $C_{10}H_{10}N_2O_2S$ (222.26): cal.: C 54.04, H 4.54, N 12.61, S 14.43. found: C 53.92, H 4.55, N 12.67, S 14.21.

EXAMPLE 9

N-[2-(3,3,3-trifluoro-1-propen-1-yl)phenylsulfonyl]-N'-(4-methoxy-6-methyl-1,3,5-triazin-2-yl)urea a) 5.0 g of 2-(3,3,3-trifluoro-1-propen-1-yl)phenysulfonamide and 1.7 g of methyl isocyanate are suspended in 25 ml of methylene chloride and 3.0 g of triethylamine are added dropwise for 10 minutes, whereupon a clear solution forms. The solution is concentrated, the residue is dissolved in a 5% sodium carbonate solution, and insoluble constituents are removed by filtration. The clear solution is acidified with 10% hydrochloric acid, to give 5.9 g of N-[2-(3,3,3-trifluoro-1-propen-1-yl)phenylsulfonyl]-N'-methylurea as a colorless precipitate with a melting point of 190°–192° C.

b) 5.9 g of N-[2-(3,3,3-trifluoro-1-propen-1-yl)phenylsulfonyl]-N'-methylurea are suspended in 100 ml of chlorobenzene. The solution is dried by refluxing it in a water separator. Then 6 g of phosgene are introduced into the reaction mixture over 20 minutes at 120°–130° C. The solvent is removed by evaporation, affording 5.6 g of 2-(3,3,3-trifluoro-1-propen-1-yl)phenylsulfonyl isocyanate as a yellowish oil.

c) 5.6 g of 2-(3,3,3-trifluoro-1-propen-1-yl)phenylsulfonyl isocyanate and 2.5 g of 2-amino-4-methoxy-6-methyl-1,3,5-triazine are stirred in absolute dioxan for 3 hours at 70°–80° C. After it has been cooled to 20° C., the reaction mixture is filtered and the clear solution so obtained is concentrated to a quarter of its volume. Then 50 ml of ether are added and 5.0 g of N-[2-(3,3,3-trifluoro-1-propen-1-yl)phenylsulfonyl]-N'-(4-methoxy-6-methyl-1,3,5-triazin-2-yl)urea crystallise from the solution. Melting point: 154°–155° C.

The intermediates and final products listed in the following table are obtained in corresponding manner.

TABLE 1

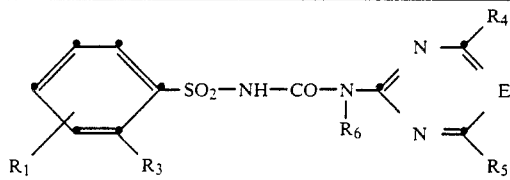

| No. | $R_1$ | $R_3$ | $R_4$ | $R_5$ | $R_6$ | E | Physical data |
|---|---|---|---|---|---|---|---|
| 1.1 | H | —CH=CH—CF₃ | CH₃ | OCH₃ | H | N | m.p. 159–160° C. |
| 1.2 | H | —CH=CH—CF₃ | OCH₃ | OCH₃ | H | N | m.p. 185–186° C. |
| 1.3 | H | —CH=CH—CF₃ | CH₃ | OCH₃ | H | CH | m.p. 166–169° C. |
| 1.4 | H | —CH=CH—CF₃ | CH₃ | CH₃ | H | CH | m.p. 186–189° C. |
| 1.5 | H | —CH=CH—CF₃ | CH₃ | OCHF₂ | H | CH | m.p. 178–179° C. |
| 1.6 | H | —CH=CH—CF₃ | OCH₃ | OCH₃ | H | CH | m.p. 185–186° C. |
| 1.7 | H | —CH=CH—CF₃ | OCH₃ | —OCH₂—CF₃ | H | N | m.p. 151–152° C. |
| 1.8 | H | —CH=CH—CF₃ | OCH₃ | —N(CH₃)₂ | H | N | m.p. 174–175° C. |
| 1.9 | H | —CH=CH—CF₃ | OCH₃ | —N(CH₃)₂ | H | CH | |
| 1.10 | H | —CH=CH—CF₃ | Cl | OCHF₂ | H | CH | |
| 1.11 | H | —CH=CH—CF₃ | OCHF₂ | —N(CH₃)₂ | H | CH | |
| 1.12 | H | —CH=CH—CF₃ | Cl | OCH₃ | H | CH | m.p. 174–175° C. |
| 1.13 | H | —CH=CH—CF₃ | OCH₃ | OCH₃ | CH₃ | CH | |
| 1.14 | H | —CH=CH—CH₂—CN | CH₃ | OCH₃ | H | H | m.p. 139–141° C. |
| 1.15 | H | —CH=CH—CH₂—CN | CH₃ | CH₃ | H | CH | |
| 1.16 | H | —CH=CH—CH₂—CN | OCH₃ | OCH₃ | H | CH | |
| 1.17 | H | —CH=CH—CH₂—CN | OCH₃ | CH₃ | H | CH | |
| 1.18 | H | —CH=CH—CH₂—CN | OCH₃ | OCH₃ | H | N | |
| 1.19 | H | —CH=CH—CH₂—O—CO—CH₃ | CH₃ | CH₃ | H | CH | |
| 1.20 | H | —CH=CH—CH₂—O—CO—CH₃ | CH₃ | OCH₃ | H | CH | m.p. 144–146° C. |
| 1.21 | H | —CH=CH—CH₂—O—CO—CH₃ | OCH₃ | OCH₃ | H | CH | |
| 1.22 | H | —CH=CH—CH₂—O—CO—CH₃ | CH₃ | OCH₃ | H | N | m.p. 128–129° C. |
| 1.23 | H | —CH=CH—CH₂—O—CO—CH₃ | OCH₃ | OCH₃ | H | N | |
| 1.24 | H | —CH=CH—OCH₃ | CH₃ | CH₃ | H | CH | |
| 1.25 | H | —CH=CH—OCH₃ | CH₃ | OCH₃ | H | CH | |
| 1.26 | H | —CH=CH—OCH₃ | OCH₃ | OCH₃ | H | CH | |
| 1.27 | H | —CH=CH—OCH₃ | CH₃ | OCH₃ | H | N | |
| 1.28 | H | —CH=CH—OCH₃ | OCH₃ | OCH₃ | H | N | |
| 1.29 | H | —CBr=CBr—CH₃ | CH₃ | CH₃ | H | CH | |
| 1.30 | H | —CBr=CBr—CH₃ | CH₃ | OCH₃ | H | CH | m.p. 206° C. (decomp.) |
| 1.31 | H | —CBr=CBr—CH₃ | OCH₃ | OCH₃ | H | CH | |
| 1.32 | H | —CBr=CBr—CH₃ | CH₃ | OCH₃ | H | N | m.p. 170–172° C. (decomp.) |
| 1.33 | H | —CBr=CBr—CH₃ | OCH₃ | OCH₃ | H | N | |
| 1.34 | H | —CH=CH—CH₂F | CH₃ | CH₃ | H | CH | |
| 1.35 | H | —CH=CH—CH₂F | CH₃ | OCH₃ | H | CH | |
| 1.36 | H | —CH=CH—CH₂F | OCH₃ | OCH₃ | H | CH | |
| 1.37 | H | —CH=CH—CH₂F | CH₃ | OCH₃ | H | N | |
| 1.38 | H | —CH=CH—CH₂F | OCH₃ | OCH₃ | H | N | |
| 1.39 | H | —CH=CH—COOCH₃ | CH₃ | CH₃ | H | CH | m.p. 157–158° C. |
| 1.40 | H | —CH=CH—COOCH₃ | CH₃ | OCH₃ | H | CH | m.p. 152–153° C. |
| 1.41 | H | —CH=CH—COOCH₃ | OCH₃ | OCH₃ | H | CH | |
| 1.42 | H | —CH=CH—COOCH₃ | CH₃ | OCH₃ | H | N | m.p. 154–155° C. |
| 1.43 | H | —CH=CH—COOCH₃ | OCH₃ | OCH₃ | H | N | |
| 1.44 | H | —CH=C(CH₃)—COOC₂H₅ | CH₃ | CH₃ | H | CH | |
| 1.45 | H | —CH=C(CH₃)—COOC₂H₅ | CH₃ | OCH₃ | H | CH | m.p. 161–162° C. |
| 1.46 | H | —CH=C(CH₃)—COOC₂H₅ | OCH₃ | OCH₃ | H | CH | |
| 1.47 | H | —CH=C(CH₃)—COOC₂H₅ | CH₃ | OCH₃ | H | N | |

TABLE 1-continued

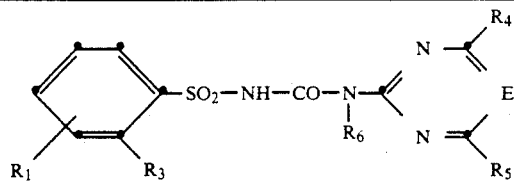

| No. | $R_1$ | $R_3$ | $R_4$ | $R_5$ | $R_6$ | E | Physical data |
|---|---|---|---|---|---|---|---|
| 1.48 | H | $-CH=C(CH_3)-COOC_2H_5$ | $OCH_3$ | $OCH_3$ | H | N | |
| 1.49 | H | $-CCl=CH-CF_3$ | $CH_3$ | $CH_3$ | H | CH | |
| 1.50 | H | $-CCl=CH-CF_3$ | $CH_3$ | $OCH_3$ | H | CH | |
| 1.51 | H | $-CCl=CH-CF_3$ | $OCH_3$ | $OCH_3$ | H | CH | |
| 1.52 | H | $-CCl=CH-CF_3$ | $CH_3$ | $OCH_3$ | H | N | |
| 1.53 | H | $-CCl=CH-CF_3$ | $OCH_3$ | $OCH_3$ | H | N | |
| 1.54 | H | $-CH=CH-CHF_2$ | $CH_3$ | $CH_3$ | H | CH | |
| 1.55 | H | $-CH=CH-CHF_2$ | $CH_3$ | $OCH_3$ | H | CH | |
| 1.56 | H | $-CH=CH-CHF_2$ | $OCH_3$ | $OCH_3$ | H | CH | |
| 1.57 | H | $-CH=CH-CHF_2$ | $CH_3$ | $OCH_3$ | H | N | |
| 1.58 | H | $-CH=CH-CHF_2$ | $OCH_3$ | $OCH_3$ | H | N | |
| 1.59 | H | $-CH=CH-NO_2$ | $CH_3$ | $CH_3$ | H | CH | |
| 1.60 | H | $-CH=CH-NO_2$ | $CH_3$ | $OCH_3$ | H | CH | |
| 1.61 | H | $-CH=CH-NO_2$ | $OCH_3$ | $OCH_3$ | H | CH | |
| 1.62 | H | $-CH=CH-NO_2$ | $CH_3$ | $OCH_3$ | H | N | |
| 1.63 | H | $-CH=CH-NO_2$ | $OCH_3$ | $OCH_3$ | H | N | |
| 1.64 | H | $-CH=CH-SO_2-N(CH_3)_2$ | $CH_3$ | $CH_3$ | H | CH | |
| 1.65 | H | $-CH=CH-SO_2-N(CH_3)_2$ | $CH_3$ | $OCH_3$ | H | CH | |
| 1.66 | H | $-CH=CH-SO_2-N(CH_3)_2$ | $OCH_3$ | $OCH_3$ | H | CH | |
| 1.67 | H | $-CH=CH-SO_2-N(CH_3)_2$ | $CH_3$ | $OCH_3$ | H | N | |
| 1.68 | H | $-CH=CH-SO_2-N(CH_3)_2$ | $OCH_3$ | $OCH_3$ | H | N | |
| 1.69 | H | $-CH=CH-SO_2-CH_3$ | $CH_3$ | $CH_3$ | H | CH | |
| 1.70 | H | $-CH=CH-SO_2-CH_3$ | $CH_3$ | $OCH_2$ | H | CH | |
| 1.71 | H | $-CH=CH-SO_2-CH_3$ | $OCH_3$ | $OCH_3$ | H | CH | |
| 1.72 | H | $-CH=CH-SO_2-CH_3$ | $CH_3$ | $OCH_3$ | H | N | m.p. 193-194° C. |
| 1.73 | H | $-CH=CH-SO_2-CH_3$ | $OCH_3$ | $OCH_3$ | H | N | |
| 1.74 | H | $-CH=CF_2$ | $CH_3$ | $CH_3$ | H | CH | |
| 1.75 | H | $-CH=CF_2$ | $CH_3$ | $OCH_3$ | H | CH | |
| 1.76 | H | $-CH=CF_2$ | $OCH_3$ | $OCH_3$ | H | CH | |
| 1.77 | H | $-CH=CF_2$ | $CH_3$ | $OCH_3$ | H | N | |
| 1.78 | H | $-CH=CF_2$ | $OCH_3$ | $OCH_3$ | H | N | |
| 1.79 | 6-F | $-CH=CH-CF_3$ | $CH_3$ | $CH_3$ | H | CH | |
| 1.80 | 6-F | $-CH=CH-CF_3$ | $CH_3$ | $OCH_3$ | H | CH | |
| 1.81 | 6-F | $-CH=CH-CF_3$ | $OCH_3$ | $OCH_3$ | H | CH | |
| 1.82 | 6-F | $-CH=CH-CF_3$ | $CH_3$ | $OCH_3$ | H | N | |
| 1.83 | 6-F | $-CH=CH-CF_3$ | $OCH_3$ | $OCH_3$ | H | N | |
| 1.84 | 5-F | $-CH=CH-CF_3$ | $CH_3$ | $CH_3$ | H | CH | |
| 1.85 | 5-F | $-CH=CH-CF_3$ | $CH_3$ | $OCH_3$ | J | CH | |
| 1.86 | 5-F | $-CH=CH-CF_3$ | $OCH_3$ | $OCH_3$ | H | CH | |
| 1.87 | 5-F | $-CH=CH-CF_3$ | $CH_3$ | $OCH_3$ | H | N | |
| 1.88 | 5-F | $-CH=CH-CF_3$ | $OCH_3$ | $OCH_3$ | H | N | |
| 1.89 | 3-F | $-CH=CH-CF_3$ | $CH_3$ | $CH_3$ | H | CH | |
| 1.90 | 3-F | $-CH=CH-CF_3$ | $CH_3$ | $OCH_3$ | H | CH | |
| 1.91 | 3-F | $-CH=CH-CF_3$ | $OCH_3$ | $OCH_3$ | H | CH | |
| 1.92 | 3-F | $-CH=CH-CF_3$ | $CH_3$ | $OCH_3$ | H | N | |
| 1.93 | 3-F | $-CH=CH-CF_3$ | $OCH_3$ | $OCH_3$ | H | N | |
| 1.94 | H | $-CH=CH-COOC_2H_5$ | $CH_3$ | $CH_3$ | H | CH | m.p. 133-134° C. |
| 1.95 | H | $-CH=CH-COOC_2H_5$ | $CH_3$ | $OCH_3$ | H | CH | m.p. 157-158° C. |
| 1.96 | H | $-CH=CH-COOC_2H_5$ | $OCH_3$ | $OCH_3$ | H | CH | |
| 1.97 | H | $-CH=CH-COOC_2H_5$ | $CH_3$ | $OCH_3$ | H | N | m.p. 147-149° C. |
| 1.98 | H | $-CH=CH-COOC_2H_5$ | $OCH_3$ | $OCH_3$ | H | N | |
| 1.99 | H | $-CH=CH-C_6F_{13}$-n | $CH_3$ | $CH_3$ | H | CH | m.p. 134-138° C. |
| 1.100 | H | $-CH=CH-C_6F_{13}$-n | $CH_3$ | $OCH_3$ | H | CH | m.p. 114-116° C. |
| 1.101 | H | $-CH=CH-C_6F_{13}$-n | $OCH_3$ | $OCH_3$ | H | CH | |
| 1.102 | H | $-CH=CH-C_6F_{13}$-n | $CH_3$ | $OCH_3$ | H | N | m.p. 133-136° C. |
| 1.103 | H | $-CH=CH-C_6F_{13}$-n | $OCH_3$ | $OCH_3$ | H | N | |
| 1.104 | H | $-CH=CH-CH(CH_3)-O-CO-CH_3$ | $CH_3$ | $CH_3$ | H | CH | |
| 1.105 | H | $-CH=CH-CH(CH_3)-O-CO-CH_3$ | $CH_3$ | $OCH_3$ | H | CH | |
| 1.106 | H | $-CH=CH-CH(CH_3)-O-CO-CH_3$ | $OCH_3$ | $OCH_3$ | H | CH | |
| 1.107 | H | $-CH=CH-CH(CH_3)-O-CO-CH_3$ | $CH_3$ | $OCH_3$ | H | N | m.p.117-118° C. |
| 1.108 | H | $-CH=CH-CH(CH_3)-O-CO-CH_3$ | $OCH_3$ | $OCH_3$ | H | N | |
| 1.109 | H | $-CH=CH-C_3F_7$-n | $CH_3$ | $OCH_3$ | H | N | m.p. 128-130° C. |
| 1.110 | H | $-CH=CH-CF_2-CH_3$ | $CH_3$ | $OCH_3$ | H | N | m.p. 162-163° C. |
| 1.111 | H | $-CH=C(CF_3)-CH_2CF_3$ | $CH_3$ | $OCH_3$ | H | N | m.p. 164-165° C. |
| 1.112 | H | $-CH=CH-CN$ | $CH_3$ | $OCH_3$ | H | CH | m.p. 157° C. (decomp.) |
| 1.113 | H | $-CH=C(CH_3)-CF_3$ | $CH_3$ | $OCH_3$ | H | CH | m.p. 161-162° C. |
| 1.114 | H | $-CH=CH-CH_2OH$ | $CH_3$ | $OCH_3$ | H | CH | m.p. 141° C. (decomp.) |
| 1.115 | H | $-CH=CH-CF_3$ | $CH_3$ | $OC_2H_5$ | H | N | m.p. 146-149° C. |
| 1.116 | H | $-CH=CH-Br$ | $CH_3$ | $OCH_3$ | H | N | m.p. 153-154° C. |
| 1.117 | H | $-CH=CH-SO_2-CF_3$ | $CH_3$ | $OCH_3$ | H | N | m.p. 174-175° C. |
| 1.118 | H | $-CH=CH-SO-CF_3$ | $CH_3$ | $OCH_3$ | H | N | m.p. 177-178° C. |
| 1.119 | H | $-CH=CH-CO-CH_3$ | $CH_3$ | $OCH_3$ | H | N | m.p. 155-156° C. |

TABLE 1-continued

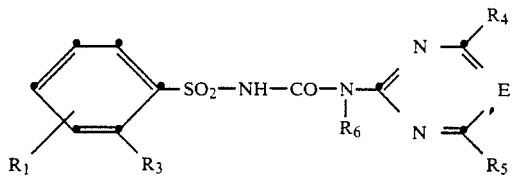

| No. | R1 | R3 | R4 | R5 | R6 | E | Physical data |
|---|---|---|---|---|---|---|---|
| 1.120 | H | $-CH=CHC_3F_7n$ | $OCH_3$ | $OCH_3$ | H | N | |
| 1.121 | H | $-CH=CHC_3F_7n$ | $CH_3$ | $OCH_3$ | H | CH | |
| 1.122 | H | $-CH=CHC_3F_7n$ | $OCH_3$ | $OCH_3$ | H | CH | |
| 1.123 | H | $-CH=CHCF_2-CH_3$ | $OCH_3$ | $OCH_3$ | H | N | |
| 1.124 | H | $-CH=CH-CF_2-CH_3$ | $OCH_3$ | $CH_3$ | H | CH | |
| 1.125 | H | $-CH=CH-CF_2-CH_3$ | $OCH_3$ | $OCH_3$ | H | CH | |
| 1.126 | H | $-CH=CH-CN$ | $OCH_3$ | $OCH_3$ | H | N | |
| 1.127 | H | $-CH=CH-CN$ | $CH_3$ | $OCH_3$ | H | CH | |
| 1.128 | H | $-CH=CH-CN$ | $OCH_3$ | $OCH_3$ | H | CH | |
| 1.129 | H | $-CH=CH-CH_2-OH$ | $CH_3$ | $OCH_3$ | H | N | |
| 1.130 | H | $-CH=CH-CH_2-OH$ | $CH_3$ | $OCH_3$ | H | CH | |
| 1.131 | H | $-CH=CH-CH_2-OH$ | $OCH_3$ | $OCH_3$ | H | CH | |
| 1.132 | H | $-CH=CH-CF_3$ | $OCH_3$ | $OCHF_2$ | H | CH | |
| 1.133 | H | $-CH=CH-CF_3$ | $OCHF_2$ | $OCHF_2$ | H | CH | |
| 1.134 | H | $-CH=CH-CF_3$ | $OCH_3$ | $OCH_2CH_3$ | H | N | |
| 1.135 | H | $-CH=CH-CF_3$ | $OCH_2CH_3$ | $OCH_2CH_3$ | H | N | |
| 1.136 | H | $-CH=CH-CF_3$ | $CH_2CH_3$ | $OCH_3$ | H | N | |
| 1.137 | H | $-CH=CH-Br$ | $OCH_3$ | $OCH_3$ | H | N | |
| 1.138 | H | $-CH=CH-Br$ | $OCH_3$ | $OCH_3$ | H | CH | |
| 1.139 | H | $-CH=CH-Br$ | $CH_3$ | $OCH_3$ | H | CH | |
| 1.140 | H | $-CH=CH-SO_2-CF_3$ | $OCH_3$ | $OCH_3$ | H | N | |
| 1.141 | H | $-CH=CH-SO_2-CF_3$ | $CH_3$ | $OCH_3$ | H | CH | |
| 1.142 | H | $-CH=CH-SO_2-CF_3$ | $OCH_3$ | $OCH_3$ | H | CH | |
| 1.143 | H | $-CH=CH-COCH_3$ | $OCH_3$ | $OCH_3$ | H | N | |
| 1.144 | H | $-CH=CH-COCH_3$ | $CH_3$ | $OCH_3$ | H | CH | |
| 1.145 | H | $-CH=CH-COCH_3$ | $OCH_3$ | $OCH_3$ | H | CH | |
| 1.146 | 5-$CH_3$ | $-CH=CH-CF_3$ | $CH_3$ | $OCH_3$ | H | N | m.p. 161–163° C. |
| 1.147 | 5-$CH_3$ | $-CH=CH-CF_3$ | $OCH_3$ | $OCH_3$ | H | N | |
| 1.148 | 5-$CH_3$ | $-CH=CH-CF_3$ | $CH_3$ | $OCH_3$ | H | CH | |
| 1.149 | 5-$CH_3$ | $-CH=CH-CF_3$ | $OCH_3$ | $OCH_3$ | H | CH | |
| 1.150 | 5-$NO_2$ | $-CH=CH-CF_3$ | $CH_3$ | $OCH_3$ | H | N | m.p. 170–172° C. |
| 1.151 | 5-$NO_2$ | $-CH=CH-CF_3$ | $OCH_3$ | $OCH_3$ | H | N | |
| 1.152 | 5-$NO_2$ | $-CH=CH-CF_3$ | $CH_3$ | $OCH_3$ | H | CH | |
| 1.153 | 5-$NO_2$ | $-CH=CH-CF_3$ | $OCH_3$ | $OCH_3$ | H | CH | |
| 1.154 | H | $-CH=CH-CH_2-OCH_3$ | $CH_3$ | $OCH_3$ | H | N | |
| 1.155 | H | $-CH=CH-CH_2-OCH_3$ | $CH_3$ | $OCH_3$ | H | N | |
| 1.156 | H | $-CH=CH-CH_2-OCH_3$ | $OCH_3$ | $CH_3$ | H | CH | |
| 1.157 | H | $-CH=CH-CH_2-OCH_3$ | $OCH_3$ | $OCH_3$ | H | CH | |
| 1.158 | H | $-CBr=CHBr$ | $CH_3$ | $OCH_3$ | H | N | |
| 1.159 | H | $-CBr=CHBr$ | $OCH_3$ | $OCH_3$ | H | N | |
| 1.160 | H | $-CBr=CHBr$ | $CH_3$ | $OCH_3$ | H | CH | |
| 1.161 | H | $-CBr=CHBr$ | $OCH_3$ | $OCH_3$ | H | CH | |

TABLE 2

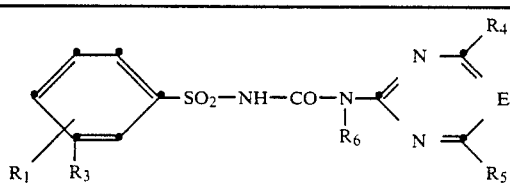

| No. | R1 | R3 | R4 | R5 | R6 | E | Physical data |
|---|---|---|---|---|---|---|---|
| 2.1 | H | $-CH=CH-COOC_2H_5$ | $CH_3$ | $OCH_3$ | H | N | m.p. 196–198° C. |
| 2.2 | H | $-CH=CH-COOC_2H_5$ | $CH_3$ | $CH_3$ | H | CH | m.p. 204–205° C. |
| 2.3 | H | $-CH=CH-CF_3$ | $CH_3$ | $OCH_3$ | H | N | m.p. 161–162° C. |
| 2.4 | H | $-CH=CH-CF_3$ | $CH_3$ | $OCH_3$ | H | CH | |
| 2.5 | H | $-CH=CH-CF_3$ | $CH_3$ | $OCH_3$ | H | CH | |
| 2.6 | H | $-CH=CH-CF_3$ | $OCH_3$ | $OCH_3$ | H | N | |

TABLE 3

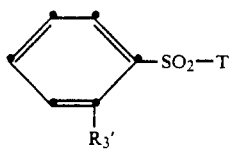

| No. | R₃' | T | Physical data |
|---|---|---|---|
| 3.1 | —CH=C(CH₃)—COOC₂H₅ | NH₂ | oil |
| 3.2 | —CH=CH—CF₃ | NH₂ | m.p. 153–154° C. |
| 3.3 | —CH=CH—CF₃ | —NH—CO—NHCH₃ | m.p. 190–192° C. |
| 3.4 | —CH=CH—CF₃ | —N=C=O | oil |
| 3.5 | —CH=CH—CF₃ | —NH—CO—OC₆H₅ | |
| 3.6 | —CH=CH—CH₂—CN | NH₂ | m.p. 144–145° C. |
| 3.7 | —CH=CH—CH₂—O—CO—CH₃ | NH₂ | m.p. 94–95° C. |
| 3.8 | —CH=CH—C₆F₁₃-n | NH₂ | m.p. 60–61° C. |
| 3.9 | —CH=CH—CH(CH₃)—O—CO—CH₃ | NH₂ | m.p. 67–69° C. |
| 3.10 | —CH=CH—C₃F₇-n | NH₂ | m.p. 63–64° C. |
| 3.11 | —CH=CH—CF₂CH₃ | NH₂ | m.p. 105–106° C. |
| 3.12 | —CH=C(CF₃)—CH₂—CF₃ | NH₂ | |
| 3.13 | —CH=CH—CN | NH₂ | |
| 3.14 | —CH=C(CH₃)—CF₃ | NH₂ | |
| 3.15 | —CH=CH—CH₂OH | NH₂ | m.p. 116–117° C. |
| 3.16 | —CH=CHBr | NH₂ | m.p. 150–151° C. |
| 3.17 | —CH=CH—SO₂—CF₃ | NH₂ | |
| 3.18 | —CH=CH—CO—CH₃ | NH₂ | |
| 3.19 | —CH=CH—SO—CF₃ | NH₂ | |
| 3.20 | —CH=CH—NO₂ | Cl | m.p. 90–92° C. |
| 3.21 | —CH=CH—CF₂ | Cl | m.p. 43–44° C. |
| 3.22 | —CH=CH—CH₂—OCO—CH₃ | Cl | |
| 3.23 | —CH=CH—C₃F₇-n | Cl | |
| 3.24 | —CH=CHBr | Cl | |
| 3.25 | —CH=CF₂ | Cl | |
| 3.26 | —CH=CF₂ | NH₂ | |
| 3.27 | —CH=CF₂ | —N=C=O | |
| 3.28 | —CBr=CBr—CH₃ | NH₂ | m.p. 209° C. |
| 3.29 | —CBr=CHBr | NH₂ | |

TABLE 4

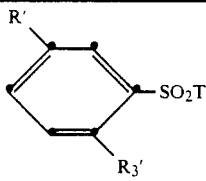

| No. | R₁ | R₃' | T | Physical data |
|---|---|---|---|---|
| 4.1 | CH₃ | —CH=CH—CF₃ | NH₂ | m.p. 153–154° C. |
| 4.2 | NO₂ | —CH=CH—CF₃ | NH₂ | m.p. 176–178° C. |
| 4.3 | C₂H₅ | —CH=CH—CF₃ | NH₂ | |
| 4.4 | C₂H₅ | —CH=CH—CF₃ | —N=C=O | |
| 4.5 | NO₂ | —CH=CH—CN | NH₂ | |

EXAMPLE 10

Formulation Examples for Compounds of Formula I
(Percentages are by Weight)

| (a) Wettable powders | (a) | (b) | (c) |
|---|---|---|---|
| Compound of formula I | 20% | 60% | 0.5% |
| sodium lignosulfonate | 5% | 5% | 5% |
| sodium laurylsulfate | 3% | — | — |
| sodium diisobutylnaphthalenesulfonate | — | 6% | 6% |
| octylphenol polyethylene glycol ether (7–8 moles of ethylene oxide) | — | 2% | 2% |
| highly dispersed silicid acid | 5% | 27% | 27% |
| kaolin | 67% | — | — |
| sodium chloride | — | — | 59.5% |

The active ingredient is thoroughly mixed with the adjuvants and the mixture is thoroughly ground in a suitable mill, affording wettable powders which can be diluted with water to give suspensions of the desired concentration.

| (b) Emulsifiable concentrates | (a) | (b) |
|---|---|---|
| Compound of formula I | 10% | 1% |
| octylphenol polyethylene glycol ether (4–5 moles of ethylene oxide) | 3% | 3% |
| calcium dodecylbenzenesulfonate castor oil polyglycol ether (36 moles of ethylene oxide) | 4% | 4% |
| cyclohexanone | 30% | 10% |
| xylene mixture | 50% | 79% |

Emulsions of any required concentration can be obtained from this concentrate by dilution with water.

| (c) Dusts | (a) | (b) |
|---|---|---|
| Compound of formula I | 0.1% | 1% |
| talcum | 99.9% | — |
| kaolin | — | 99% |

Dusts which are ready for use are obtained by mixing the active ingredient with the carriers, and grinding the mixture in a suitable mill.

| (d) Extruder granulate | (a) | (b) |
|---|---|---|
| Compound of formula I | 10% | 1% |
| sodium lignosulfonate | 2% | 2% |
| carboxymethylcellulose | 1% | 1% |
| kaolin | 87% | 96% |

The active ingredient is mixed and ground with the adjuvants, and the mixture is subsequently moistened with water. The mixture is extruded and then dried in a stream of air.

| (e) Coated granulate | |
|---|---|
| Compound of formula I | 3% |
| polyethylene glycol 200 | 2% |
| kaolin | 94% |

The finely ground active ingredient is uniformly applied, in a mixer, to the kaolin moistened with polyethylene glycol. Non-dusty coated granulates are obtained in this manner.

| (f) Suspension concentrate | (a) | (b) |
|---|---|---|
| Compound of formula I | 40% | 5% |
| ethylene glycol | 10% | 10% |
| nonylphenol polyethylene glycol ether (15 moles of ethylene oxide) | 6% | 1% |
| sodium lignosulfonate | 10% | 5% |
| carboxymethylcellulose | 1% | 1% |
| 37% aqueous formaldehyde solutions | 0.2% | 0.2% |
| silocone oil in the form of a 75% aueous emulsion | 0.8% | 0.8% |
| water | 32% | 77% |

The finely ground active ingredient is intimately mixed with the adjuvants, giving a suspension concentrate from which suspensions of any desired concentration can be obtained by dilution with water.

| (g) Salt solution | |
|---|---|
| Compound of formula I | 5% |
| isopropylamine | 1% |
| octylphenol polyethylene glykol ether (78 moles of ethylene oxide) | 3% |
| water | 91% |

BIOLOGICAL EXAMPLES

EXAMPLE 11

Preemergence Herbicidal Action

Plastic pots are filled with expanded vermiculite (density: 0.135 g/cm$^3$, water-absorbing capacity: 0.565 1/1). After the non-adsorptive vermiculite has been saturated with an aqueous emulsion in deionised water which contains the test compound in a concentration of 70.8 ppm, seeds of the following plants are sown on the surface: Nasturtium officinalis, Agrostis tenuis, Stellaria media and Digitaria sanguinalis. The pots are then kept in a climatic chamber at 20° C., an illumination of about 20 lux and a relative humidity of 70%. During the germinating phase of 4 to 5 days, the pots are covered with lightpermeable material and watered with deionised water to increase the local humidity. After the 5th day, 0.5% of a commercial liquid fertiliser (Greenzit ®) is added to the water. The test is evaluated 12 days after sowing and the action on the plants is assessed according to the following rating:

1: plants have not emerged or are totally withered
2-3: very pronounced action
4-6: medium action
7-8: weak action
9: no action (as untreated controls).

Preemergence Action

Concentration of the test compound emulsion: 70.8 ppm

| | Test plant | | | |
|---|---|---|---|---|
| Compound | Nasturtium | Stellaria | Agrostis | Digitaria |
| 1.1 | 2 | 1 | 2 | 2 |
| 1.2 | 2 | 2 | 6 | 7 |
| 1.3 | 1 | 1 | 1 | 1 |
| 1.4 | 1 | 2 | 1 | 2 |
| 1.5 | 2 | 3 | 2 | 5 |
| 1.6 | 2 | 2 | 2 | 4 |
| 1.7 | 2 | 2 | 5 | 7 |
| 1.12 | 1 | 2 | 1 | 3 |
| 1.14 | 1 | 2 | 1 | 1 |
| 1.20 | 1 | 1 | 1 | 1 |
| 1.22 | 2 | 2 | 2 | 3 |
| 1.30 | 1 | 2 | 1 | 2 |
| 1.32 | 2 | 2 | 3 | 5 |
| 1.39 | 2 | 5 | 2 | 5 |
| 1.40 | 2 | 2 | 1 | 2 |
| 1.42 | 4 | 3 | 7 | 5 |
| 1.45 | 2 | 1 | 2 | 2 |
| 1.94 | 2 | 4 | 2 | 5 |
| 1.95 | 1 | 1 | 1 | 2 |
| 1.97 | 2 | 2 | 2 | 3 |
| 1.99 | 5 | 2 | 6 | 2 |
| 1.107 | 2 | 2 | 2 | 2 |
| 1.109 | 4 | 2 | 6 | 7 |
| 1.110 | 3 | 3 | 3 | 4 |
| 1.112 | 1 | 3 | 1 | 3 |
| 1.113 | 1 | 3 | 1 | 4 |
| 1.114 | 2 | 2 | 2 | 2 |
| 1.115 | 2 | 2 | 2 | 3 |
| 1.116 | 2 | 1 | 2 | 2 |
| 2.1 | 4 | 4 | 4 | 5 |
| 2.2 | 5 | 4 | 5 | 6 |
| 2.3 | 2 | 2 | 2 | 6 |

EXAMPLE 12

Test of Selectivity in Preemergence Application

Using the test procedure of Example 10, a large number of plant seeds are treated with test substance of different rates of application. Evaluation is made in accordance with the same rating.

Preemergence Action:

| Action rate of application in kg a.i/ha Test plant | Compound 1.1 | |
|---|---|---|
| | 0.125 | 0.06 |
| maize | 8 | 9 |
| wheat | 9 | 9 |
| Alopecurus myos. | 3 | 4 |
| Cyperus escul. | 3 | 4 |
| Rottboellia ex. | 5 | 5 |
| Abutilon | 2 | 2 |
| Xanthium Sp. | 2 | 2 |
| Chenopodium Sp. | 2 | 2 |
| Ipomoea | 2 | 3 |
| Sinapis | 2 | 2 |
| Galium aparine | 2 | 2 |
| Viola tricolor | 2 | 2 |

EXAMPLE 13

Postemergence Herbicidal Action (Contact Action)

A number of weeds and cultivated plants, both monocots and dicots, are sprayed postemergence, in the 4- to 6-leaf stage, with an aqueous dispersion of test compound at a rate of application of 0.5 kg a.i./ha, and then kept at 24° to 26° and 45 to 60% relative humidity. The test is evaluated 15 days after treatment using the same rating as in the preemergence test.

Postemergence Action

Rate of application: 0.5 kg/ha

| Compound | Avena | Setaria | Lolium | Solanum | Sinapis | Stellaria | Phaseolus |
|---|---|---|---|---|---|---|---|
| 1.1 | 4 | 4 | 3 | 2 | 2 | 2 | 3 |
| 1.14 | 7 | 7 | 4 | 3 | 2 | 2 | 3 |
| 1.22 | 9 | 7 | 7 | 5 | 2 | 3 | 3 |
| 1.45* | 6 | 5 | 5 | 4 | 2 | 3 | 5 |

*4 kg of active ingredient/hectare

EXAMPLE 14

Test of Selectivity in Postemergence Application

Using the same test procedure as in Example 12, a large number of plants are treated with test substance at different rates of application. Evaluation is made in accordance with the rating of Example 10.

Postemergence Action

| Action Rate of application in kg a.i./ha Test plant | Compound 1.1 | |
|---|---|---|
| | 0.250 | 0.125 |
| wheat | 9 | 9 |
| maize | 7 | 9 |
| dry rice | 8 | 8 |
| Cyperus escul. | 3 | 4 |
| Abutilon | 3 | 4 |
| Xanthium Sp. | 3 | 4 |
| Chenopodium Sp. | 2 | 2 |
| Sinapis | 3 | 3 |
| Galium aparine | 3 | 4 |
| Viola tricolor | 2 | 3 |

EXAMPLE 15

Growth Inhibition of Tropical Cover Crops

The test plants (*Centrosema plumieri* and *Centrosema pubescens*) are reared until fully grown and then cut back to a height of 60 cm. The plants are sprayed 7 days later with an aqueous emulsion of the test compound. The test plants are kept at 70% relative humidity and 6000 lux artificial light for 14 hours per day, at day temperatures of 27° C. and night temperatures of 21° C. The test is evaluated 4 weeks after application by assessing and weighing the new growth compared with controls and by determining the phytotoxicity.

In this test a marked reduction in new growth of the plants treated with compounds of the formula I is observed (less than 20% of the new growth of untreated control plants), without damage being caused to the test plants.

EXAMPLE 16

Growth Regulation of Soybeans

Soybeans of the "Hark" variety are sonw in plastic containers in an earth/peat/sand mixture in the ratio 6:3:1. The containers are put into a climatic chamber and the plants develop to the 5-6 trefoil leaf stage after about 5 weeks by optimum control of temperature, light, fertiliser addition, and watering. The plants are then sprayed with an aqueous mixture of a compound of the formula I until thoroughly wetted. The concentration of test compound is up to 100 g a.i./ha. Evaluation is made about 5 weeks after application. Compared with untreated controls, the compounds of the formula I effect a substantial increase in the number and weight of the harvested siliques on the leading shoot.

EXAMPLE 17

Growth Inhibition of Cereals

Summar barley (*Hordeum vulgare*) and summer rye (*Secale*) are sown in sterilised soil in plastic beakers in a greenhouse and watered as required. The cereal shoots are treated about 21 days after sowing with an aqueous spray mixture of a compound of the formula I. The concentration of test compound corresponds to a rate of application of up to 100 g of active ingredient per hectare. Evaluation of the growth of the cereals is made 21 days after application. Compared with untreated controls, the new growth of plants treated with compounds of the formula I is reduced (60-90% of the controls) and in some cases the diameter of the stalks is increased.

EXAMPLE 18

Growth Inhibition of Grasses

Seeds of the grasses *Lolium perenne, Poa pratensis, Festuca ovina*, and *Cynodon dactylon* are sown in plastic dishes filled with an earth/peat/sand mixture (6:3:1), in a greenhouse, and watered as required. The emergent grasses are cut back weekly to a height of 4 cm, and about 50 days after sowing and 1 day after the last cut are sprayed with an aqueous spray mixture oc a compound of the formula I. The concentration of test compound corresponds to a rate of application of up to 100 g of active ingredient per hectare. The growth of the grasses is evaluated 21 days after application. The evaluation shows that the compounds of formula I effect a reduction in growth of 10-30% compared with untreated controls.

What is claimed is:

1. A compound of the formula IIa

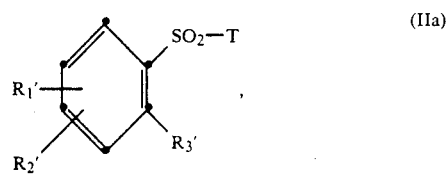

wherein
T is $-N=C=O$ or $-NHT_4$,
$R_1'$ is hydrogen, halogen, $C_1-C_5$alkyl, $C_1-C_4$haloalkyl, $C_1-C_4$alkoxy, $-CONR_9R_{10}$ or $-NO_2$,
$R_2'$ is hydrogen, halogen, $C_1-C_4$alkyl, $C_1-C_4$haloalkyl, $C_1-C_4$alkoxy, $C_1-C_4$haloalkoxy or alkoxyalkyl containing not more than 4 carbon atoms,
$R_3'$ is a $-C(T_1)=C(T_2)(T_3)$ group,
$T_1$ is hydrogen, $C_1-C_4$alkyl, cyano,
$T_2$ is $-CONR_9R_{10}$, $-CH_2-C_1-C_4$alkoxy, $-CH(-C_1-C_4$alkyl$)-C_1-C_4$alkoxy, $-CH_2-CN$, $-S(O)_q-C_1-C_3$alkyl, $-S(O)_q-C_1-C_3$haloalkyl, where q is 0, 1 or 2, $-COR_8$, or $C_1-C_8$alkyl which is substituted by one or more fluorine atoms,
$T_3$ is hydrogen, or $C_1-C_5$alkyl which is unsubstituted or substituted by fluorine atoms, and
$T_4$ is hydrogen, the alkyl groups $T_1$, $T_2$ and $T_3$ together containing not more than 8 carbon atoms and, $R_8$ is $C_1-C_4$alkyl, $C_1-C_4$haloalkyl or $C_2$-C-

$_6$alkoxyalkyl, $R_9$ and $R_{10}$, each independently of the other, are hydrogen or $C_1$–$C_3$alkyl.

2. A compound of the formula IIa according to claim 1, wherein one of $T_1$ and $T_2$, preferably $T_1$, is hydrogen and T is an amino group.

3. 2-(3,3,3-Trifluoro-1-propen-1-yl)phenylsulfonamide according to claim 1.

* * * * *